US009176132B2

(12) United States Patent
Fujimoto et al.

(10) Patent No.: US 9,176,132 B2
(45) Date of Patent: Nov. 3, 2015

(54) METHOD OF CALIBRATION

(71) Applicant: DAINIPPON SCREEN MFG. CO., LTD., Kyoto (JP)

(72) Inventors: Hiroki Fujimoto, Kyoto (JP); Sanzo Moriwaki, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 0 days.

(21) Appl. No.: 14/169,827

(22) Filed: Jan. 31, 2014

(65) Prior Publication Data

US 2014/0220592 A1 Aug. 7, 2014

(30) Foreign Application Priority Data

Feb. 1, 2013 (JP) .................................. 2013-018440

(51) Int. Cl.
*G01N 21/00* (2006.01)
*G01N 33/569* (2006.01)
*G01N 21/59* (2006.01)

(52) U.S. Cl.
CPC .......... *G01N 33/569* (2013.01); *G01N 21/5907* (2013.01); *G01N 2021/5969* (2013.01)

(58) Field of Classification Search
CPC ............. G06T 7/602; G06T 2207/10056; G06T 7/0012; G06T 2207/10016; G06T 2207/20068; G06T 2207/20136; G06T 7/0083; G06T 2207/30072; G06T 1/0007; G06T 2207/10024; G06T 2207/30242
See application file for complete search history.

(56) References Cited

U.S. PATENT DOCUMENTS

| 7,718,131 | B2 | 5/2010 | Jiang ........................ 422/82.08 |
| 2001/0041347 | A1* | 11/2001 | Sammak et al. ............. 435/7.23 |
| 2008/0045394 | A1* | 2/2008 | Kolenbrander et al. .......... 494/7 |
| 2012/0262704 | A1* | 10/2012 | Zahniser et al. ................ 356/39 |
| 2013/0023007 | A1* | 1/2013 | Zahniser et al. ................ 435/34 |
| 2013/0077085 | A1* | 3/2013 | Zahniser et al. ................ 356/39 |

FOREIGN PATENT DOCUMENTS

| JP | 2001-512824 | 8/2001 |
| JP | 2010-510812 | 4/2010 |
| JP | 2013-027368 | 2/2013 |
| WO | WO 99/08091 | 2/1999 |
| WO | WO 2009/066964 A1 | 5/2009 |
| WO | WO 2012/142496 A1 | 10/2012 |

OTHER PUBLICATIONS

Japanese Office Action dated Jan. 14, 2015 corresponding to Japanese Patent Application No. 2013-018440 with English translation.

* cited by examiner

*Primary Examiner* — Michael P Stafira
(74) *Attorney, Agent, or Firm* — Ostrolenk Faber LLP

(57) ABSTRACT

The following processes are performed to improve the accuracy of the process of estimating the volume of a cell clump from an image including the cell clump. First, the image including the cell clump is acquired, and the optical density of the cell clump in the image is measured. Cross-section information about the cell clump is acquired by observation using a confocal microscope or by physical cutting. Based on the cross-section information, the vertical height of the cell clump is determined. Thereafter, data representing a relationship between the aforementioned optical density and the height is acquired. This improves the accuracy of the process of converting the optical density into the height to thereby achieve the accurate estimation of the volume of the cell clump.

9 Claims, 10 Drawing Sheets

| OPTICAL DENSITY | HEIGHT |
|---|---|
| ○○○ | ☐☐☐ |
| ○○○ | ☐☐☐ |
| ○○○ | ☐☐☐ |
| ○○○ | ☐☐☐ |
| ○○○ | ☐☐☐ |
| ○○○ | ☐☐☐ |

METHOD OF CALIBRATION

BACKGROUND OF THE INVENTION

1. Field of the Invention

The present invention relates to a method of calibration for improving the accuracy of the process of estimating the volume of a cell clump from an image including the cell clump.

2. Description of the Background Art

A screening which narrows down compounds serving as candidates for medical and pharmaceutical products is performed in the course of research and development of the medical and pharmaceutical products. An example of the screening includes the steps of: preparing a plurality of culture solutions into which biological cells are put; adding compounds to the culture solutions while changing various conditions to cultivate the cells; and narrowing down the compounds serving as candidates for medical and pharmaceutical products, based on the culture states of the cells.

In such a screening, a reagent has been hitherto used for the assessment of the culture states of the cells. Specifically, a reagent is applied to the cells to cause a chemical reaction between specific molecules in the cells and the reagent. The culture states of the cells are judged by absorbance measurement of such optical changes. This method, however, has required the costly reagent, and also has required much time for the chemical reaction. In addition, this method has been incapable of observing changes in the same cell with time because the reagent destroys cell walls.

In recent years, three-dimensional culture such that cells are cultivated in three dimensions has been performed to investigate the effects of medical and pharmaceutical products in an environment closer to that in a living body. An important object to be observed in such three-dimensional culture is the state of a spheroid that is a cell clump comprised of a group of three-dimensionally aggregated cells. However, the use of the absorbance measurement for the observation of such a cell clump gives rise to problems in requiring the costly reagent, in requiring much time for the chemical reaction and in being incapable of observing changes with time, as in the aforementioned cases.

To solve such problems, an attempt has been made in recent years to develop an apparatus for observing the culture states of cell clumps by photographing the cell clumps at a high resolution without using any reagent. This apparatus photographs a well plate having a plurality of depressions or wells for culture at predetermined time intervals to clip images of each of the wells from the resultant photographed images. The culture states of the cell clumps in each well are assessed by displaying the clipped images on a display part and then comparing and analyzing the clipped images.

Conventional apparatuses for performing image processing by acquiring the images of cells are disclosed, for example, in Japanese Patent Application Laid-Open No. 2010-510812, Japanese Patent Application Laid-Open No. 2001-512824, and U.S. Pat. No. 7,718,131.

An important indicator for the assessment of the culture state of a cell clump is the volume of the cell clump. Thus, the development of the technique of estimating the volume of a cell clump from the image of the cell clump has been advanced especially in recent years. An example of the process of estimating the volume of a cell clump includes: converting the optical density of the cell clump in an image into the height thereof; and calculating the volume of the cell clump, based on the height after the conversion and the area of the cell clump.

However, a relationship between the optical density of pixels in the image and the height of the cell clump varies depending on the type and culturing conditions of cells. To determine the volume of a cell clump with accuracy, it is preferable that the relationship between the optical density of the pixels and the height of the cell clump is adjusted by calibration for each object to be observed.

SUMMARY OF THE INVENTION

It is therefore an object of the present invention to provide a method of calibration for improving the accuracy of the process of estimating the volume of a cell clump from an image including the cell clump.

According to an aspect of the present invention, a method of calibration for improving the accuracy of the process of estimating the volume of a cell clump from an image including the cell clump comprises the steps of: a) directing light from one of a first position lying over a cell clump held in a well having a bottom portion at least which is pervious to light and a second position lying under the cell clump toward the other of the first and second positions to receive the light at an imaging device disposed in the other of the first and second positions, thereby acquiring an image including the cell clump; b) measuring the optical density of the cell clump in the image acquired in the step a); c) acquiring cross-section information about the cell clump held in the well to determine the vertical height of the cell clump, based on the cross-section information; and d) acquiring data representing a relationship between the optical density measured in the step b) and the height determined in the step c).

The method according the aspect of the present invention acquires the data representing the relationship between the optical density of the cell clump in the image and the height of the cell clump determined based on the cross-section information to thereby improve the accuracy of the process of converting the optical density into the height. As a result, this achieves the accurate estimation of the volume of the cell clump.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 shows an example of correlation data;

DESCRIPTION OF THE PREFERRED EMBODIMENTS

A preferred embodiment according to the present invention will now be described with reference to the drawings.

<1. Configuration of Image Acquisition Apparatus>

Figure 1:
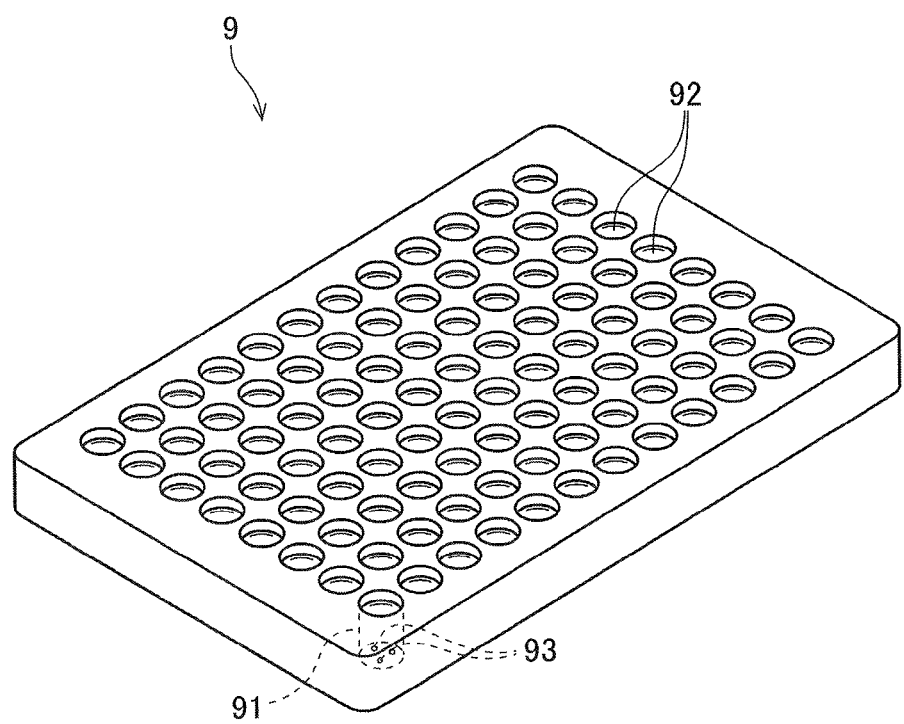
FIG. 1 is a perspective view showing an example of a well plate.

FIG. 1 is a perspective view showing an example of a well plate 9 to be set in an image acquisition apparatus 1. The well plate 9 is a generally plate-shaped specimen container having a plurality of depressions or wells 91. An example of the material of the well plate 9 includes a transparent resin. Thus, at least a bottom portion of each of the wells 91 allows light to pass therethrough in a vertical direction. As shown in FIG. 1, the wells 91 are arranged regularly in the upper surface of the well plate 9. Multiple cell clumps 93 referred to as spheroids are held with a culture solution 92 in each of the wells 91. Compounds with different concentrations and different compositions are added to the culture solution 92 in the wells 91.

Figure 2:
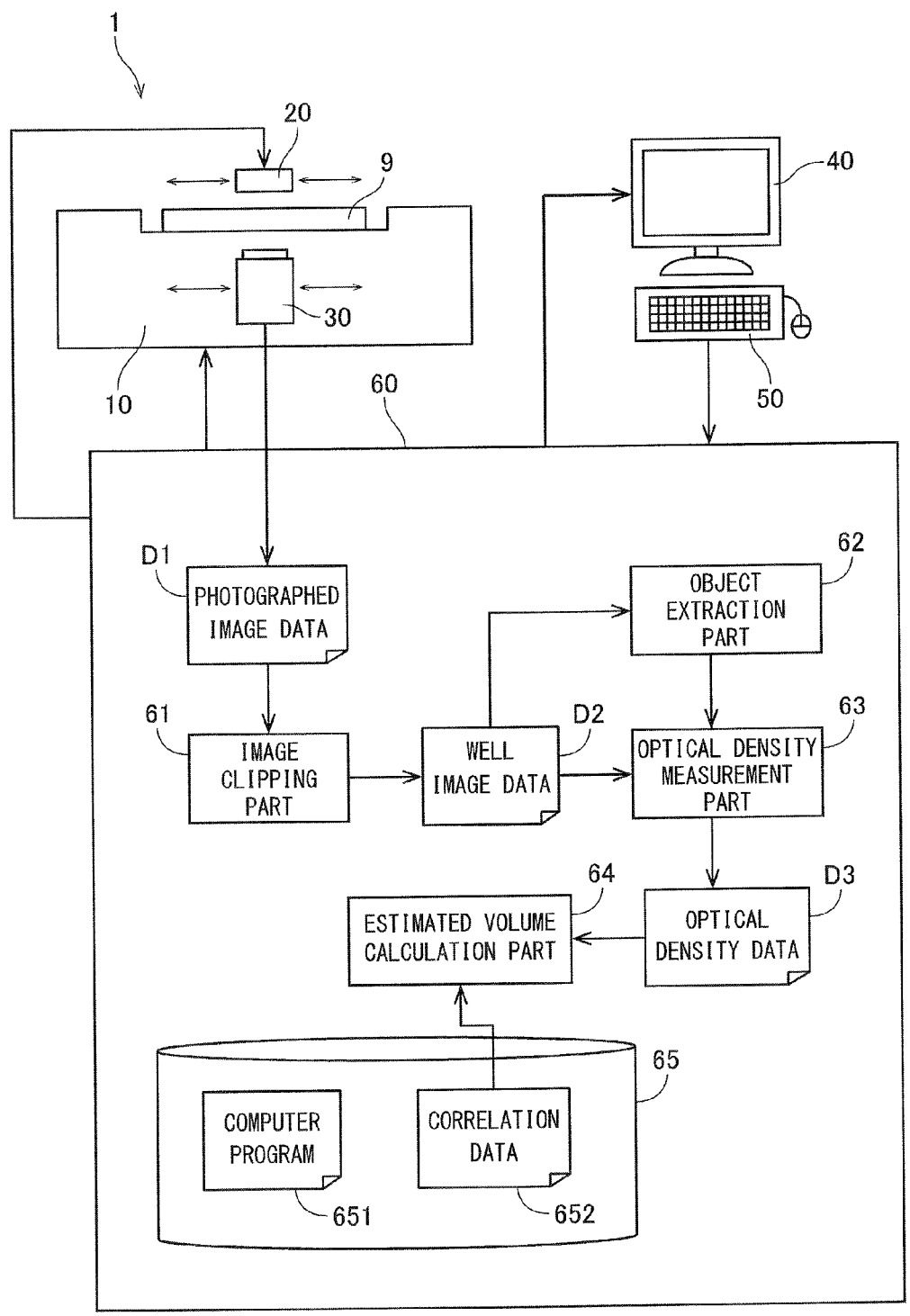
FIG. 2 conceptually shows a configuration of an image acquisition apparatus.

FIG. 2 conceptually shows a configuration of the image acquisition apparatus 1 to which a method of calibration according to the preferred embodiment of the present invention is applied. The image acquisition apparatus 1 is an apparatus for acquiring images of the cell clumps 93 cultivated in the well plate 9. The image acquisition apparatus 1 is used, for example, for a screening step for narrowing down compounds serving as candidates for medical and pharmaceutical products in the field of research and development of the medical and pharmaceutical products. An operator for the screening step uses the image acquisition apparatus 1 to acquire image data about the well plate 9. Then, the operator compares and analyzes the culture states of the cell clumps 93 in the wells 91, based on the acquired image data, to verify the effects of the compounds added to the culture solution 92.

As shown in FIG. 2, the image acquisition apparatus 1 according to the present preferred embodiment includes a plate holder 10, a light emitting part 20, an imaging part 30, a display part 40, an input part 50 and a computer 60. The plate holder 10, the light emitting part 20, the imaging part 30, the display part 40 and the input part 50 are electrically connected to the computer 60.

The plate holder 10 is a table for holding the well plate 9 thereon. The well plate 9 in a horizontal attitude with the bottom thereof downside is set on the plate holder 10. The light emitting part 20 and the imaging part 30 are disposed respectively over and under the well plate 9 held on the plate holder 10. The light emitting part 20 directs light downwardly from over the well plate 9. The imaging part 30 is implemented, for example, by a line sensor or an area sensor which includes an optical system such as a lens, and an imaging device such as CCD, CMOS and other imaging devices.

The image acquisition apparatus 1 further includes a drive mechanism not shown for moving the light emitting part 20 and the imaging part 30 laterally. The drive mechanism includes, for example, a motor, and a power transmission mechanism such as a ball screw for transmitting the driving force of the motor. The well plate 9 is photographed in a manner to be described below. While light is directed from the light emitting part 20 toward part of the well plate 9, the imaging part 30 photographs the aforementioned part of the well plate 9. The photographing is repeated in a similar manner while the drive mechanism is operated to move the light emitting part 20 and the imaging part 30 laterally relative to the well plate 9. As a result, photographed image data D1 about the entire well plate 9 is acquired.

The light emitting part 20 may be any light emitter which directs light toward the cell clumps 93 held in the well plate 9. Thus, the light emitting part 20 may have a light source disposed in a position deviated from over the well plate 9, and be configured to direct light from the light source through an optical system such as a mirror onto the well plate 9. Also, the light emitting part 20 may be disposed under the well plate 9, whereas the imaging part 30 be disposed over the well plate 9.

The display part 40 is a section for displaying various pieces of information related to image processing in the image acquisition apparatus 1. The display part 40 displays well image data D2 and the like which will be described later. A liquid crystal display, for example, is used as the display part 40. The input part 50 is a section for inputting various commands to the computer 60. A keyboard and a mouse, for example, are used as the input part 50. A user of the image acquisition apparatus 1 may manipulate the input part 50 to enter various commands into the computer 60 while viewing the display part 40.

Both the functions of the display part 40 and the functions of the input part 50 may be implemented by a single device such as a touch panel display device.

The computer 60 functions both as a controller for controlling the operations of the aforementioned parts of the image acquisition apparatus 1 and as an image processor for estimating the volume of each cell clump 93, based on the acquired image data. The computer 60 includes a CPU and a memory. The CPU operates in accordance with a previously set computer program 651, input signals and various data, whereby the computer 60 controls the operations of the aforementioned drive mechanism, the light emitting part 20 and the imaging part 30. Thus, the photographing of the well plate 9 is performed in the image acquisition apparatus 1.

As conceptually shown in FIG. 2, the computer 60 according to the present preferred embodiment includes an image clipping part 61, an object extraction part 62, an optical density measurement part 63, an estimated volume calculation part 64, and a storage part 65. The CPU in the computer 60 performs computation processes while referencing the computer program 651 stored in the storage part 65, whereby the functions of the image clipping part 61, the object extraction part 62, the optical density measurement part 63 and the estimated volume calculation part 64 are implemented.

The storage part 65 is a section for storing therein various data handled in the image acquisition apparatus 1. The storage part 65 is implemented by a storage device including a hard disk drive, a RAM and the like, for example. The storage part 65 may be part of hardware constituting the computer 60, as shown in FIG. 2, or be an external storage device connected to the computer 60.

The aforementioned computer program 651 is stored in the storage part 65. The computer program 651 is read from a computer-readable storage medium including a CD, a DVD and the like, for example, and is stored in the storage part 65. Correlation data 652 for reference during the execution of a volume estimation process to be described later is also stored in the storage part 65 according to the present preferred embodiment. The correlation data 652 includes a relationship between the optical densities of the cell clumps 93 in image data and the heights of the cell clumps 93 which is held as rewritable data.

<2. Volume Estimation Process>

Figure 3:
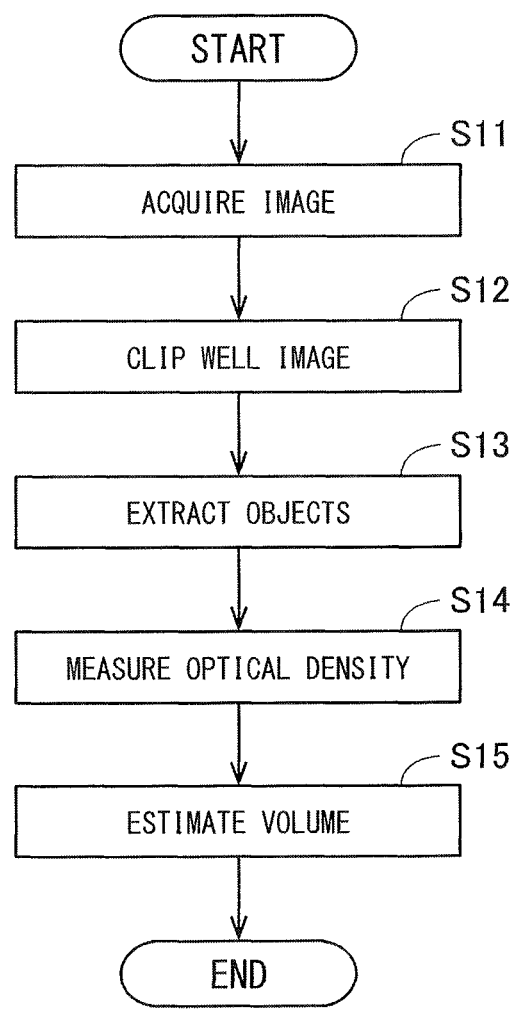
FIG. 3 is a flow diagram showing a procedure of a volume estimation process.

FIG. 3 is a flow diagram showing a procedure of the process of estimating the volume of a cell clump 93 to be observed in the image acquisition apparatus 1. The computer 60 operates the image clipping part 61, the object extraction part 62, the optical density measurement part 63 and the estimated volume calculation part 64 while referencing an input signal from the input part 50, the computer program 651 and the correlation data 652, whereby the process shown in FIG. 3 is executed. The procedure of the process will be described hereinafter with reference to FIGS. 2 and 3.

For the estimation of the volume of a cell clump 93, the well plate 9 is initially photographed, so that the photographed image data D1 is acquired (in Step S11). Specifically, while light is directed from the light emitting part 20 toward part of the well plate 9, the imaging part 30 receives the light. Thus, the aforementioned part of the well plate 9 is photographed. Then, while the light emitting part 20 and the imaging part 30 are moved laterally, the photographing is repeated in a similar manner. As a result, the photographed image data D1 about the entire well plate 9 is acquired.

Upon being acquired in the imaging part 30, the photographed image data D1 is inputted to the image clipping part 61 in the computer 60. The image clipping part 61 clips image data about each of the wells 91 from the photographed image data D1 (in Step S12). The image data about each of the wells 91 is referred to as "well image data D2" hereinafter.

Figure 4:
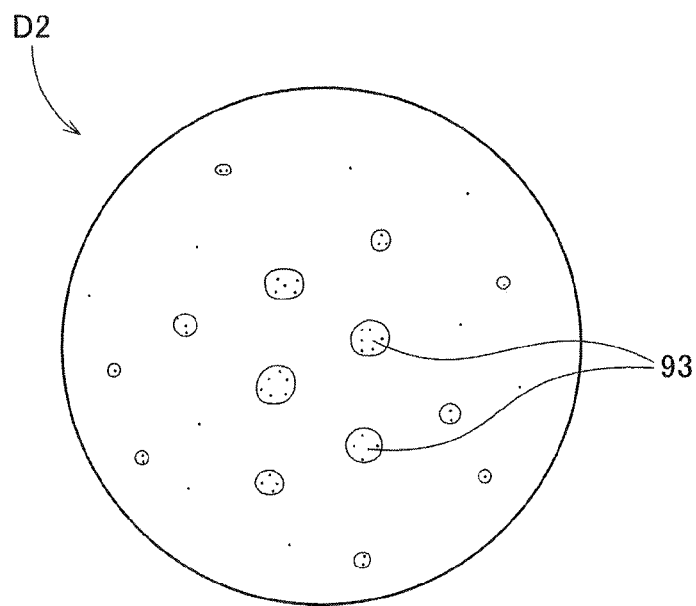
FIGS. 4 and 5 are views showing examples of well image data displayed on a display part.

Each well image data D2 which is clipped is displayed on the display part 40. FIG. 4 is a view showing an example of the well image data D2 displayed on the display part 40. In the example of FIG. 4, the image of a plurality of cell clumps 93 is included in the single well image data D2. It should be noted that the number of cell clumps 93 included in the single well image data D2 may be only one. The intensity of light directed from the light emitting part 20 is attenuated when the light passes through the cell clumps 93. Thus, the optical density of each cell clump 93 in the well image data D2 is higher than that of other portions of the well image data D2 where the cell clumps 93 are absent.

Next, the object extraction part 62 performs the process of extracting objects 930 corresponding to the cell clumps 93 from the well image data D2 (in Step S13). The process of extracting the objects 930 is performed, for example, by extracting pixels having optical densities higher than a previously set threshold value from the well image data D2. The threshold value of the optical density for use in the extraction of the objects 930 may be changed by making entries, depending on whether the result of extraction is appropriate or not.

Figure 5:
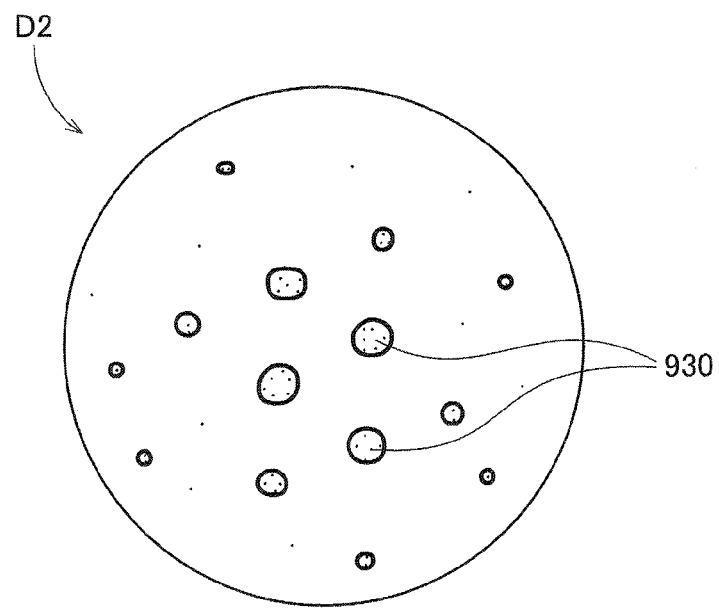

FIG. 5 is a view showing an example of the well image data D2 displayed on the display part 40 after the extraction of the objects 930. In the example of FIG. 5, the outlines of the extracted objects 930 are highlighted with thick solid lines. This makes it easy to visually distinguish between the objects 930 and other portions.

Figure 6:
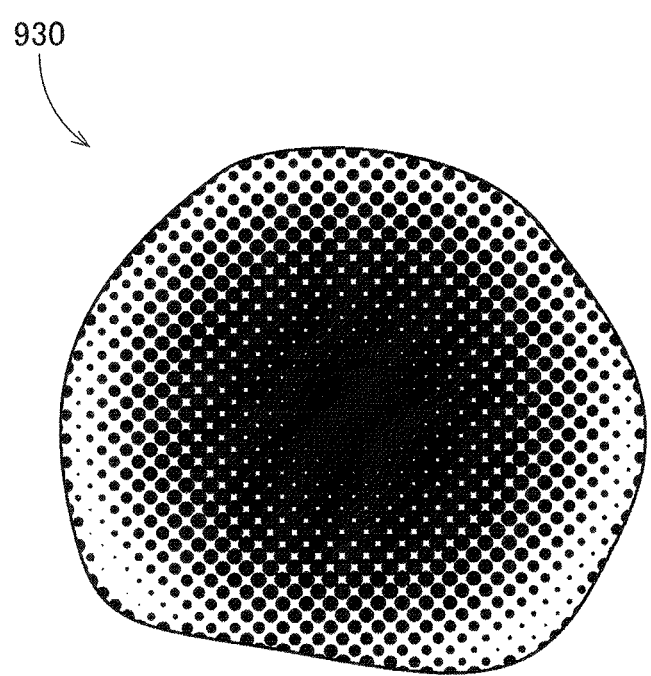
FIG. 6 is a view showing a single object on an enlarged scale.

Subsequently, the optical density of each of the objects 930 in the well image data D2 is measured (in Step S14). FIG. 6 is a view showing a single object 930 on an enlarged scale. As indicated by halftone dots in FIG. 6, the object 930 has an optical density distribution dependent on the amount of light transmission. Specifically, a portion of a cell clump 93 which is lower in height is greater in the amount of light transmission and is accordingly relatively low in optical density. A portion of the cell clump 93 which is greater in height is smaller in the amount of light transmission and is accordingly relatively high in optical density.

In Step S14, the optical density measurement part 63 measures the optical density of each of the pixels constituting an object 930. This provides optical density data D3 representing the optical density distribution of the aforementioned object 930. Also, the optical density measurement part 63 similarly acquires the optical density data D3 about each of the objects 930 included in the well image data D2.

Figure 7:
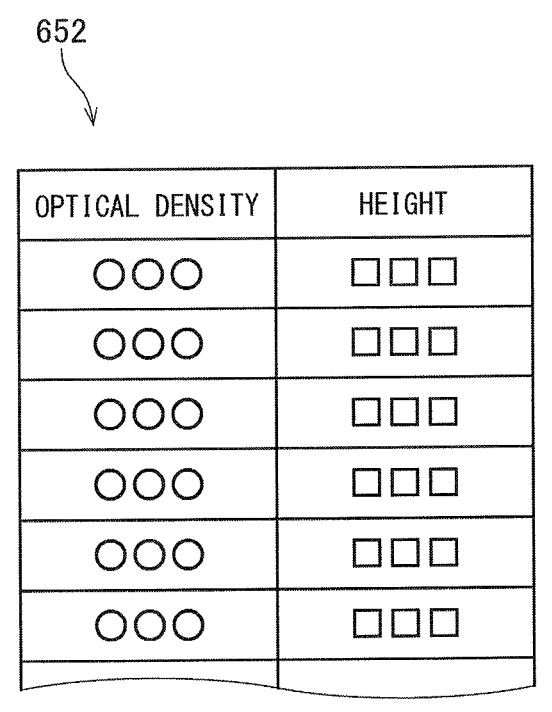

Thereafter, the volume of each object 930 is estimated, based on the acquired optical density data D3 (in Step S15). In this step, the estimated volume calculation part 64 initially reads the correlation data 652 from the storage part 65. FIG. 7 shows an example of the correlation data 652. As shown in FIG. 7, the correlation data 652 specifies a correspondence between the optical densities and the heights corresponding to the respective optical densities. That is, the optical densities in the left-hand column of FIG. 7 and the heights in the right-hand column of FIG. 7 are in corresponding relation.

The estimated volume calculation part 64 uses a conversion formula in accordance with the correlation data 652 to convert the optical densities included in the optical density data D3 into heights. This provides information about a height distribution of each cell clump 93. Then, the volume of each of the pixels constituting an object 930 is determined by multiplying the area of each pixel by the height thereof. Then, the volume of the cell clump 93 estimated from the object 930 is determined by adding the volumes of the respective pixels together.

The correlation data 652 illustrated in FIG. 7 is in the form of table data in which the optical densities and the heights are in a one-to-one correspondence. The correlation data 652, however, may be in other forms so long as information for converting optical densities into heights is included in the correlation data 652.

<3. Calibration Process>

Figure 8:
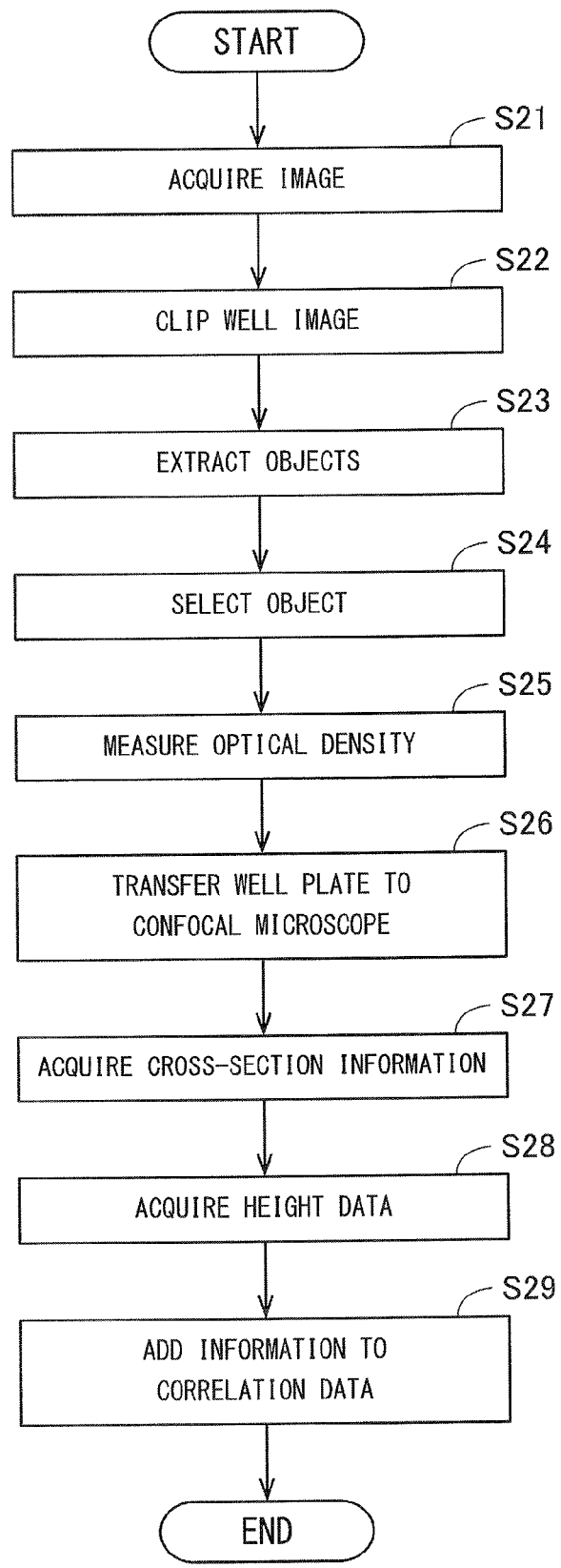
FIG. 8 is a flow diagram showing a procedure of a calibration process.

Next, a calibration process for improving the accuracy of the aforementioned volume estimation process will be described. FIG. 8 is a flow diagram showing a procedure of the calibration process.

For the calibration process, the processes of acquiring the photographed image data D1 (in Step S21), clipping the well image data D2 (in Step S22) and extracting the objects 930 (in Step S23) are initially performed in the image acquisition apparatus 1, as shown in FIG. 8. The processes in Steps S21 to S23 are similar to those in Steps S11 to S13 described above, and will not be described.

Next, at least one object 930 used for calibration is selected from among the plurality of objects 930 included in the well image data D2 (in Step S24). The selection of the at least one object 930 may be made by a user of the image acquisition apparatus 1 who manipulates the input part 50 while viewing the well image data D2 displayed on the display part 40 or be automatically made by the computer 60 based on the computer program 651.

After an object 930 is selected, the optical density of the object 930 is measured (in Step S25). In this step, the optical density measurement part 63 measures the optical density of each of the pixels constituting the object 930. This provides the optical density data D3 representing the optical density distribution of the object 930. When two or more objects 930 are selected in Step S24, the optical density measurement part 63 similarly acquires the optical density data D3 for each of the objects 930.

Figure 9:
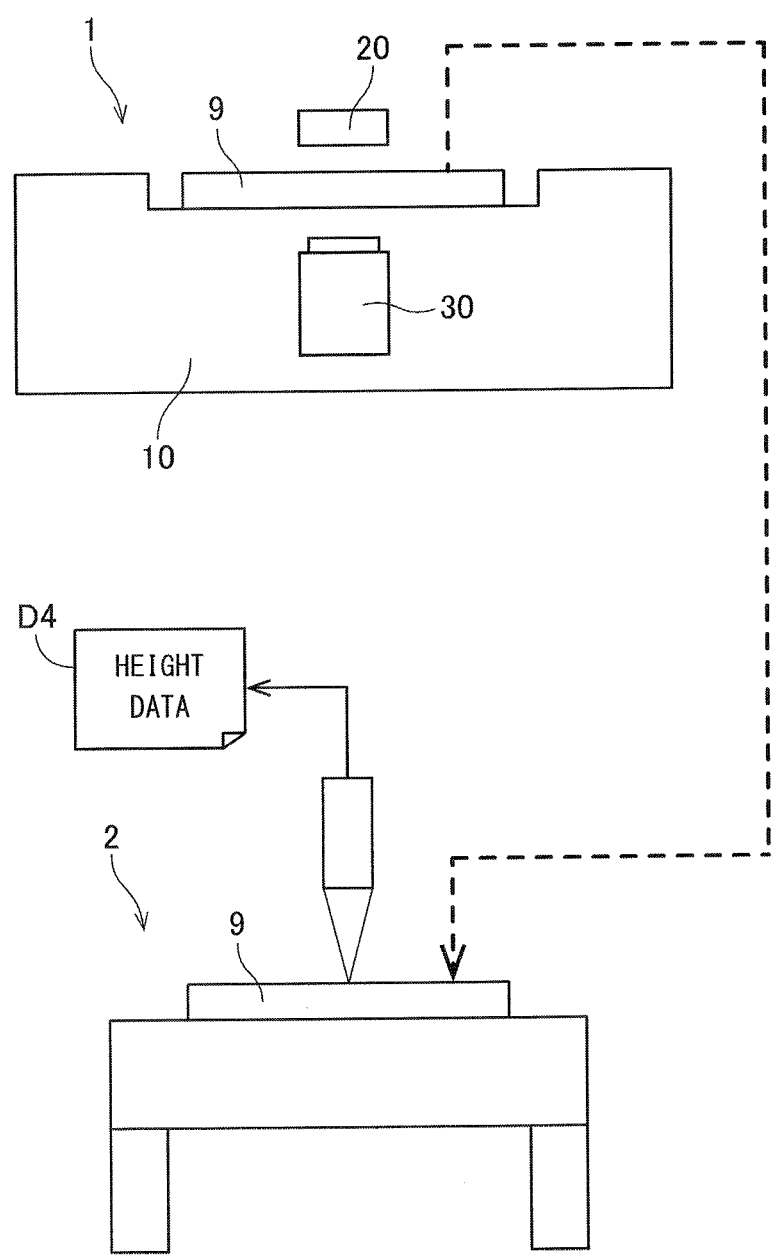
FIG. 9 conceptually shows the transfer of the well plate from the image acquisition apparatus to a confocal microscope.

Next, the user of the image acquisition apparatus 1 takes the well plate 9 out of the plate holder 10, and sets this well plate 9 on the confocal microscope 2. That is, the user transfers the well plate 9 from the image acquisition apparatus 1 to the confocal microscope 2 (in Step S26), as shown in FIG. 9. Then, the user observes the cell clump 93 corresponding to the aforementioned object 930 selected in Step S24 with the confocal microscope 2.

Figure 10:
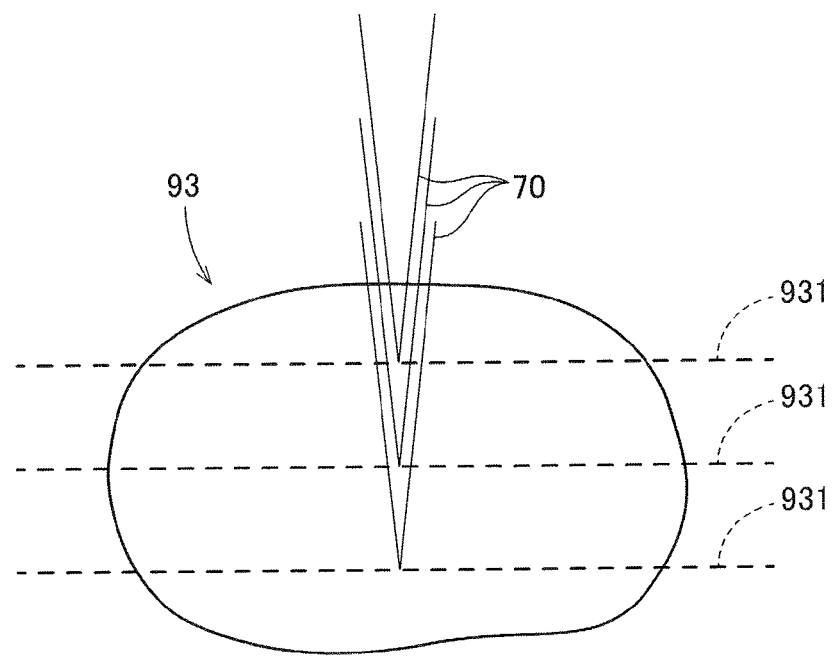
FIG. 10 is a view showing an observation with the confocal microscope.

The confocal microscope 2 is a microscope which removes light beams reflected from positions clear of the focal position and detects only light beams 70 reflected from the focal position by means of an optical system having a pinhole to clearly show images in the focal position. The confocal microscope 2 is able to change the focal position by shifting the position of a lens on the optical path. This allows the observation of the distribution of cells at a plurality of cross-sections 931 of a cell clump 93, as shown in FIG. 10. In other words, this allows the optical acquisition of a plurality of pieces of cross-section information about a single cell clump 93 (in Step S27).

After the acquisition of the plurality of pieces of cross-section information, the three-dimensional cell distribution of the entire cell clump 93 is accurately obtained. Accordingly, the vertical height of the cell clump 93 at each position is accurately obtained. As a result, height data D4 representing the height distribution of the cell clump 93 is acquired (in Step S28), as conceptually shown in FIG. 9.

After the acquisition of the height data D4, the user of the image acquisition apparatus 1 inputs the height data D4 to the computer 60 of the image acquisition apparatus 1. The height data D4 may be inputted by the user who manipulates the input part 50 or be transferred from the confocal microscope 2 through a network to the image acquisition apparatus 1.

Thus, the image acquisition apparatus 1 has acquired the optical density data D3 and the height data D4 corresponding to the optical density data D3. The computer 60 of the image acquisition apparatus 1 adds information in the optical density data D3 and the height data D4 to the correlation data 652 stored in the storage part 65 (in Step S29). Thus, new information representing the optical densities and the heights is added to the correlation data 652. As a result, calibration is performed on the correlation data 652 which is information for converting the optical densities of the cell clumps 93 in the well image data D2 into the heights of the cell clumps 93.

In the calibration process according to the present preferred embodiment as described above, the information representing the relationship between the optical densities of the cell clumps 93 in the well image data D2 and the heights of the cell clumps 93 obtained based on the cross-section information is acquired. Then, the acquired information is added to the correlation data 652. This improves the accuracy of the process of converting the optical densities into the heights to thereby achieve the accurate estimation of the volume of each cell clump 93.

In particular, the estimation with higher accuracy is achieved by performing the calibration process for each of the types and culturing conditions of the cell clump 93 to be observed to update the correlation data 652.

<4. Modifications>

While the one preferred embodiment according to the present invention has been described hereinabove, the present invention is not limited to the aforementioned preferred embodiment.

Figure 11:
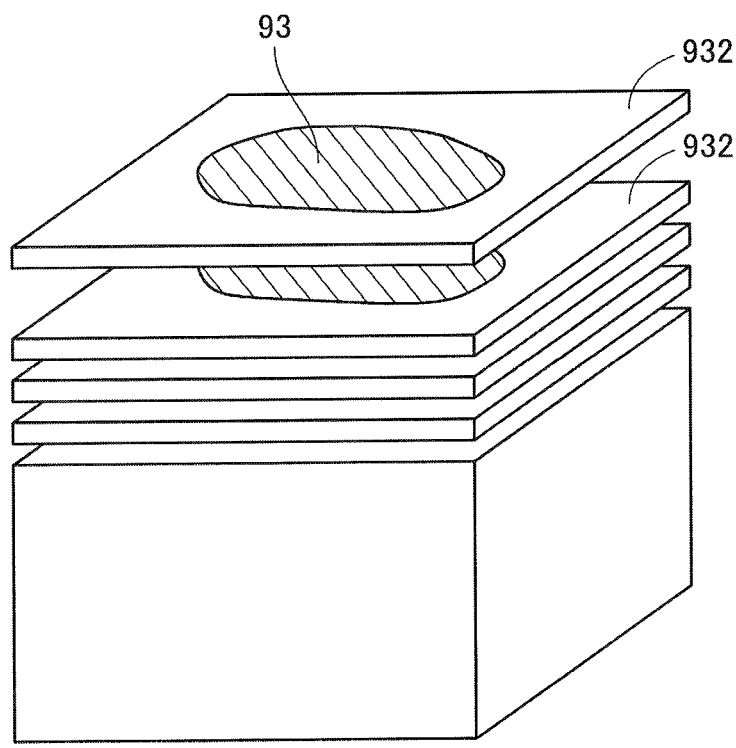
FIG. 11 is a view showing a cell clump being physically cut.

In the aforementioned preferred embodiment, the confocal microscope 2 is used to optically acquire the cross-section information about a cell clump 93. This achieves the acquisition of the cross-section information about the cell clump 93 without destruction of the cell clump 93. However, other methods may be used to acquire the cross-section information about the cell clump 93. For example, after the freezing or paraffin embedding of a cell clump 93 held in a well 91, the cell clump 93 may be physically cut into a plurality of slices 932, as shown in FIG. 11. The cutting of the cell clump 93 may be carried out, for example, with a microtome. Then, the cross-section information about the cell clump 93 may be acquired by observing each of the slices 932 with a microscope.

Before the photographing in the image acquisition apparatus 1 or the acquisition of the cross-section information, the cell clumps 93 in the wells 91 may be labeled by immunostaining using fluorescent dyes or enzymes. For example, a cell clump 93 to be observed may be fluorescently labeled by introducing a fluorescent protein which binds to specific molecules in cells into the cells. Alternatively, immunostaining based on an enzyme labeled antibody method may be performed on a cell clump 93 to be observed by using an enzyme which binds to a specific protein in cells.

The use of the immunostaining improves the visual recognizability of the cell clumps 93. In particular, the immunostaining performed before the photographing in the image acquisition apparatus 1 increases the difference in optical density between the cell clumps 93 and other portions in the well image data D2. This accordingly improves the accuracy of the process of converting the optical densities into the heights. Also, the immunostaining performed before the acquisition of the cross-section information makes it easy to recognize the distribution of cells at cross-sections. Thus, the heights of the cell clumps 93 are determined more easily.

In the calibration process according to the aforementioned preferred embodiment, the height data D4 is acquired with the confocal microscope 2 after the optical density data D3 is acquired in the image acquisition apparatus 1. In the reverse manner, the optical density data D3 may be acquired in the image acquisition apparatus 1 after the height data D4 is acquired with the confocal microscope 2. Specifically, Step S27 and S28 in FIG. 8 are performed first, and the well plate 9 is then transferred from the confocal microscope 2 to the image acquisition apparatus 1. Thereafter, Steps S21 to S25 are performed. Finally, Step S29 is performed.

The number of wells 91 included in the well plate 9 may be different from that shown in the example of FIG. 1. The shape of the wells 91 may be circular as seen in top plan view as shown in FIG. 1, or may be other shapes such as a rectangular shape.

The components described in the aforementioned preferred embodiment and in the various modifications may be consistently combined together, as appropriate.

While the invention has been described in detail, the foregoing description is in all aspects illustrative and not restrictive. It is understood that numerous other modifications and variations can be devised without departing from the scope of the invention.

What is claimed is:

1. A method of calibration for improving the accuracy of the process of estimating the volume of a cell clump from an image including the cell clump, comprising the steps of:
    a) directing light from one of a first position lying over a cell clump held in a well having a bottom portion at least which is pervious to light and a second position lying under said cell clump toward the other of the first and second positions to receive said light at an imaging device disposed in the other of the first and second positions, thereby acquiring an image including said cell clump;
    b) measuring the optical density of said cell clump in the image acquired in said step a);
    c) acquiring cross-section information about said cell clump held in said well to determine the vertical height of said cell clump, based on said cross-section information; and
    d) acquiring data representing a relationship between the optical density measured in said step b) and the height determined in said step c),
    wherein in said step c), pieces of cross-section information are acquired by acquiring a distribution of cells at each of a plurality of cross-sections of said cell clump, and determining said vertical height of said cell clump at each position, based on said pieces of cross-section information.

2. The method according to claim 1, wherein
a distribution of cells at each of said cross-sections of said cell clump held in said well is optically acquired using a confocal microscope in said step c).

3. The method according to claim 1, wherein
in said step c), a plurality of slices is formed by immobilizing said cell clump held in said well and thereafter physically cutting said cell clump, and a distribution of cells at each of said cross-sections of said cell clump is acquired by observing each of said slices.

4. The method according to claim 1, further comprising the step of
labeling said cell clump in said well by immunostaining prior to said step a).

5. The method according to claim 1, further comprising the step of
labeling said cell clump in said well by immunostaining prior to said step c).

6. The method according to claim 1, wherein:
a plurality of cell clumps are held in said well;
the optical density of at least one cell clump selected from the plurality of cell clumps included in said image is measured in said step b); and
the vertical height of said at least one cell clump is determined in said step c).

7. The method according to claim 1, wherein
a height distribution of said cell clump is determined in said step c).

8. The method according to claim 1, further comprising the step of
e) adding the data acquired in said step d) to correlation data representing a relationship between the optical density of said cell clump in said image and the height of said cell clump.

9. The method according to claim 7, wherein
said correlation data is updated for each type or each culturing condition of said cell clump.

* * * * *